: (12) United States Patent
Talasila et al.

(10) Patent No.: US 8,263,124 B2
(45) Date of Patent: Sep. 11, 2012

(54) ANTHISTAMINE-DECONGESTANT PHARMACEUTICAL COMPOSITIONS

(75) Inventors: Kamalakar Talasila, Thane (IN); Debashis Dash, Panchkula (IN); Srinivas Irukula, Hyderabad (IN); Dhanorkar Vipin Tatyasaheb, Ahmedabad (IN); Mailatur Sivaraman Mohan, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 2289 days.

(21) Appl. No.: 10/510,064

(22) PCT Filed: Apr. 4, 2002

(86) PCT No.: PCT/IB02/01068
§ 371 (c)(1),
(2), (4) Date: Feb. 13, 2006

(87) PCT Pub. No.: WO03/084510
PCT Pub. Date: Oct. 16, 2003

(65) Prior Publication Data
US 2006/0182800 A1 Aug. 17, 2006

(51) Int. Cl.
*A61K 9/22* (2006.01)
(52) U.S. Cl. ........ 424/468; 424/472; 424/474; 424/475; 514/770; 514/778; 514/781; 514/783; 514/853
(58) Field of Classification Search .................. 514/770, 514/778, 781, 783, 784, 853; 424/468, 472, 424/474, 475
See application file for complete search history.

(56) References Cited

U.S. PATENT DOCUMENTS

| | | | |
|---|---|---|---|
| 3,878,217 A | 4/1975 | Carr et al. | |
| 4,996,061 A | 2/1991 | Webb et al. | |
| 6,039,974 A | 3/2000 | MacLaren et al. | |
| 6,210,712 B1* | 4/2001 | Edgren et al. | 424/473 |
| 6,267,986 B1 | 7/2001 | Jain et al. | |
| 6,627,646 B2* | 9/2003 | Bakale et al. | 514/322 |
| 2005/0256163 A1* | 11/2005 | Kor et al. | 514/317 |

FOREIGN PATENT DOCUMENTS

| | | |
|---|---|---|
| WO | 99/09957 A1 | 3/1999 |
| WO | 01/85148 A2 | 11/2001 |
| WO | 01/94313 A2 | 12/2001 |
| WO | 02/080857 A2 | 10/2002 |

OTHER PUBLICATIONS

Muzaffar et al. "Polymorphism and drug availability" J. Phar. 1(1) 59-66 (1979).*
Jain et al. "Polymorphisom in pharmacey" Indian Drugs 23(g)315-329 (1986).*
Doelker et al. "Crystalline modification . . . " CA 138:209993 (2002).*
Doelker et al. "Physicochemical behavior or active . . . " CA 132:325872 (2000.*
Otsuka et al. "effect of polymorphic . . . " Chem. Pharm. Bull, 47(6) 852-856 (1999).*
CMU Pharmaceutical polymorphism, internat p. 1-3 (2002) (print out Apr. 3, 2008).*
Singhal et al. "Drug polymorphism . . . " Advanced drug delivery reviews 56. p. 335-347 (2004).*
Pharmcpedia "Tablet:formulation . . . " (2009) p. 1-7 internet.*
Buhler "POlyvinylpyrrolidone . . . " p. 179-183 (2009 from internet).*
Ahjel et al. :Directely compressible . . . Farmacia (2008) v. LVI(6) 591-599.*
US Pharmcopia #23, national formulary #18, p. 1843 (1995).*
Simpson, K., et al., "Fexofenadine a review of its use in the management of seasonal allergic rhinitis and chronic idiopathic urticaria", Journal of Allergy and Clinical Immunology, vol. 2, No. 59, pp. 301-321, 2000.
Sussman, G.L., et al., "The efficacy and safety of fexofenadine HCl and pseudoephedrine, alone and in combination, in seasonal allergic rhinitis", Journal of Allergy and Clinical Immunology, vol. 104, No. 1, pp. 100-106, 1999.

* cited by examiner

*Primary Examiner* — Celia Chang
(74) *Attorney, Agent, or Firm* — Gilman Pergament LLP; Milagros A. Cepeda; Edward D. Pergament

(57) ABSTRACT

The present invention relates to pharmaceutical compositions of antihistamine-decongestant combination. Specifically the invention relates to bilayered tablet formulation comprising antihistaminic decongestant combination. More specifically present invention relates to the novel polymorph of fexofenadine or pharmaceutically accepted salts thereof, with at least one decongestant in the form of bilayered tablet. The preferred polymorphs are polymorph A and polymorph X of fexofenadine hydrochloride.

20 Claims, No Drawings

ANTIHISTAMINE-DECONGESTANT PHARMACEUTICAL COMPOSITIONS

CROSS-REFERENCE TO RELATED APPLICATION

This application is a United States national phase filing of International Application No. PCT/IB02/01068, filed Apr. 4, 2002.

FIELD OF THE INVENTION

The present invention relates to the pharmaceutical composition for antihistaminic-decongestant combination in the form of unit dosage form. One of the preferred embodiments of the invention is directed towards the use of novel polymorph of Fexofenadine with at least one decongestant in the form of bilayered tablet and process of making such bilayered tablets.

DESCRIPTION OF THE RELATED ART

Antihistaminic and decongestant act by different mechanism to treat allergic reactions. Decongestants constrict vessels in the nasal mucus membranes and thereby decrease tissue swelling and nasal congestion. Decongestants are found to be better than antihistamines for restoring the potency of congested nasal airways. Histamine is a mediator released from cells, which line the walls of the nasal mucous membranes (mast cells). When released, histamine binds to local histamine receptors, thereby causing sneezing, nasal itching, swelling of the nasal membranes, and increased nasal secretions. Antihistamines relieve these effects, albeit by a different mechanism than decongestants. Antihistamines block the binding of histamines to the histamine receptors by preoccupying the histaminic receptors. Consequently they are effective only if given prior to histamine release since once histamine is released and binds to the receptors, it is too late. Although individuals typically take antihistamines after symptoms occur, it is more desirable to dose antihistamines so as to effect therapeutic availability in anticipation of histamine release.

Combining decongestants and antihistamines utilizes both mechanistic approaches, and has been shown to offer more complete relief of rhinitis symptoms than therapy with either component alone. The scientific advancement over the years has presented to the mankind the more potent and non sedating antihistamines compared to those available in old days.

U.S. Pat. No. 4,996,061 discloses the pharmaceutical composition in the form of multiple compressed tablets comprising (a) a discrete zone made with Formulation (A) which comprises a carrier base material combined with a therapeutically effective decongestant amount of a sympathomimetic drug, or a pharmaceutically acceptable salt thereof, the carrier base material being a mixture of (i) one or more pharmaceutically acceptable water-soluble nonionic cellulose ethers in an amount from about 18% to about 50% by weight of Formulation (A), (ii) one or more pharmaceutically acceptable anionic surfactants in an amount from about 2% to about 20% by weight of Formulation (A), and (iii) one or more other pharmaceutically acceptable excipients, and (b) a discrete zone made with Formulation (B) which comprises a second carrier base material combined with a therapeutically effective antihistaminic amount of a piperidinoalkanol, or a pharmaceutically acceptable salt thereof, the second carrier base being a mixture of (i) calcium carbonate in an amount from about 0.5% to about 25% by weight of Formulation (B), (ii) one or more pharmaceutically acceptable nonionic surfactants in an amount from about 1% to about 10% by weight of Formulation (B), and (iii) one or more other pharmaceutically acceptable excipients, wherein Formulation (B) optionally also contains a therapeutically effective decongestant amount of a sympathomimetic drug, or a pharmaceutically acceptable salt thereof; with the proviso that when said pharmaceutical composition is in the form of a compression-coated tablet, the inner core zone is made with Formulation (A) and the outer coat zone is made with Formulation (B).

U.S. Pat. No. 6,267,986 B1 relates to a process for the preparation of a controlled release pharmaceutical composition comprising two discrete zones wherein the first discrete zone comprises therapeutically effective amount of Pseudoephedrine or its pharmaceutically acceptable salt as active ingredient and the second discrete zone comprises a therapeutically effective amount of a long-acting antihistamine selected from the group consisting of Loratadine, Azatidine, Fexofenadine, Terfenadine, Cetirizine, Astemizole, and Levocabastine, or their pharmaceutically acceptable salt as active ingredient.

U.S. Pat. No. 6,039,974 provides a pharmaceutical composition in the form of a bilayered tablet comprising, (a) a first discrete zone made with Formulation (A) which comprises, a therapeutically effective decongestant amount of a sympathomimetic drug, or a pharmaceutically acceptable salt thereof, in an amount of about 18% to about 39% by weight of Formulation (A), and a first carrier base material, the first carrier base material comprising a mixture of; (I) carnauba wax in an amount of about 59% to about 81% by weight of Formulation (A); and (ii) a suitable antiadherent in an amount of about 0.25% to about 2.00% by weight of Formulation (A); wherein said first carrier base material provides a sustained release of the sympathomimetic drug; and (b) a second discrete zone made with Formulation (B) which comprises a therapeutically effective antihistaminic amount of a piperidinoalkanol, or a pharmaceutically acceptable salt thereof, in an amount of about 15% to about 30% by weight of Formulation (B) and a second carrier base material, the second carrier base comprising a mixture of; (I) a cellulose diluent in an amount of about 27% to about 73% by weight of Formulation (B); (ii) pregelatinized starch in an amount of about 15% to about 30% by weight of Formulation (B); (iii) a suitable disintegrant in an amount of about 0.25% to about 6.00% by weight of Formulation (B); and (iv) a suitable lubricant in an amount of about 0.25% to about 2.00% by weight of Formulation (B); wherein said second carrier base material provides an immediate release of the piperidinoalkanol or the pharmaceutically acceptable salt thereof.

Fexofenadine is disclosed in U.S. Pat. No. 3,878,217 and is know to have duration of action >24 hours. Pseudoephedrine and its salts are commonly administered orally three to four times a day for the relief of nasal congestion. The sustained and controlled release formulations of Pseudoephedrine are also available commercially.

Various sympathomimetic drugs, such as Pseudoephedrine, phenylephrine and phenylpropanolamine are recognized by those skilled in the art as therapeutic agents effective in the relief of nasal congestion and are commonly administered concomitantly with antihistamines for relief of nasal congestion associated with allergic rhinitis. These sympathomimetic drugs are generally effective when administered orally in unit dosage form on a four times a day dosage schedule wherein the unit dosage form provides immediate release of the active medicament. For example, the recommended dosage for Pseudoephedrine hydrochloride in adults is 60 mg every 6 hours (q.i.d.). In addition, unit dosage forms containing sympathomimetic drugs can be formulated to provide prolonged release of the active medicament so as to allow the effective daily dose to be administered on a less frequent dosage schedule. For example, the recommended dosage for Pseudoephedrine hydrochloride in a sustained release formulation can be 120 mg twice daily (b.i.d.).

Polymorphism is known phenomenon to formulation scientists. The processing of polymorphs and problems due to polymeric conversion has always been challenge to formulation scientists since ages. One of the key problems with handling of polymorphs is polymeric conversion, which affects the stability and organoleptic properties of the final product. It is well appreciated that lot of care and trials are needed to handle polymorphs in the formulation.

The present invention utilizes novel polymorph of Fexofenadine (Polymorph X or Polymorph A) to produce bilayered tablets containing at least one decongestant.

Kollidon SR is polyvinyl acetate and povidone based matrix-retarding agent. It is a white or slightly yellowish, free flowing powder. It consists of 80% polyvinyl acetate, 19% Povidone in a physical mixture. 0.8% SLS and 0.2% colloidal silica are used as a stabilizers. It is worth to mention that Kollidon SR can be successfully replaced by a mixture of polyvinyl acetate and Povidone.

Since polyvinyl acetate is plastic material that produces a coherent matrix under low compression forces, when tablets are introduced into gastric or intestinal fluid, the water-soluble povidone is leached out to form pores through which the active ingredient slowly diffuses outwards.

Kollidon SR contains no ionic groups and is therefore inert to drug substances. The Sustained release properties are unaffected by ions or salts. Kollidon SR has excellent compressibility and endows tablets with enormous hardness and low friability. This is due to the combination of the very plastic polyvinyl acetate and also the binding povidone.

It is surprisingly found that the Pseudoephedrine part of the two discrete zones of the bilayered tablets can prepared by direct compression method thus avoiding the necessity of other processes like wet granulation which involve substantially extra processing steps.

It is therefore an object of the present invention to prepare bilayered tablets containing novel polymorph of Fexofenadine with at least one decongestant.

It is another object of the present invention to use Kollidone SR in one of the layers of bilayered tablet to produce sustained release of Pseudoephedrine hydrochloride.

It is still another object of the present invention to provide a bilayered tablet comprising two discrete zones with first zone providing sustained release of the decongestant drug and second zone providing immediate release of the antihistaminic drug as used in this description.

One of the aspects of the present invention is to use direct compression technique to prepare bilayered tablet.

According to still another object, the present invention incorporates novel polymorphs of Fexofenadine which are economic as produced by eco-friendly process and has a particle size in the range of from about 12 to about 18 microns, more preferably from about 14 to about 16 microns.

The use of robust and simple manufacturing process to produce stable formulation of antihistaminic-decongestant combination to yield consistent quality product is also an object of the present invention.

SUMMARY OF THE INVENTION

The present invention discloses the pharmaceutical composition as bilayered tablet comprising:

(a) a first discrete zone made with Formulation (A) which comprises; a therapeutically effective amount of antihistaminic drug or, a pharmaceutically accepted salt thereof in an amount from about 10% to about 30% preferably in an amount of about 15% to about 25%, and a first carrier base material, the first carrier base material comprising, a mixture of;

(i) one or more fillers selected from cellulose derivatives in an amount from about 20% to about 45% preferably in an amount of about 30% to about 45%, starch derivatives in an amount from about 5% to about 25% preferably in an amount of about 10% to about 20%, polyols in an amount from about 10% to about 30% preferably in an amount of about 10% to about 20%, by weight of Formulation (A), (ii) an at least one disintegrant in an amount from about 4% to about 15% preferably in an amount of about 6% to about 10%, by weight of Formulation (A), (iii) an at least one pharmaceutically accepted glidants or lubricants in an amount from about 0.2% to about 3%, by weight of Formulation (A), wherein, the first carrier base material provides an immediate release of the antihistaminic drug and a pharmaceutically accepted salts thereof; and (b) a second discrete zone made with Formulation (B) which comprises; a therapeutically effective amount of a decongestant drug or, a pharmaceutically accepted salt thereof in an amount from about 20% to 40% preferably in an amount of about 25% to about 35%, and a second carrier base material, the second carrier base material comprising, a mixture of;

(i) an at least one sustained release compound in an amount from about 40% to 80% preferably in an amount of about 60% to about 75% by weight of Formulation (B), (ii) an at least one pharmaceutically accepted glidants or lubricants in an amount from about 0.2% to about 4%, by weight of Formulation (B), wherein, the second carrier base material provides the sustained release of decongestant drug or pharmaceutically accepted salts thereof.

The antihistaminic drugs are selected from the group consisting of novel polymorph of Fexofenadine, Loratadine, Terfenadine, Cetrizine or a pharmaceutically accepted salts thereof, preferably novel polymorph of Fexofenadine more preferably polymorph A or Formulation X of Fexofenadine. When antihistaminic drug is novel polymorph of fexofenadine the particle size of said novel polymorph of Fexofenadine is in the range of from about 12 to about 18 microns more preferably from about 14 to about 16 microns.

The Formulation (B) is made with psedoephedrine hydrochloride by direct compression method. It has been surprisingly observed that the granule size of the blend used to prepare this layer has a critical value of 5-15% cumulative retention on mesh #80, 10-25% cumulative retention on mesh #100 and 80-95% cumulative retention on mesh #200. The said psedoephedrine granules from which second discrete layer is made of has a LOD (loss on drying) in the range of 1.5 to 3.0% preferably 2.40%.

DETAILED DESCRIPTION OF THE INVENTION

The novel polymorphs of Fexofenadine are described below.

Novel Polymorph Form A of Fexofenadine

The Form A of Fexofenadine can be identified by the following characteristics:

a visual melting point (capillary tube) in the range of about 218-224° C.;
a melting endotherm at about 227-231° C. as determined by differential scanning calorimetry;
and an X-ray powder diffraction pattern essentially as shown in the Table1.

TABLE 1

XRD data of Fexofenadine Hydrochloride Form A polymorph

| D-Space, Angstroms d value | Intensity, $I/I_o$, % $I/Io$ |
|---|---|
| 23.11 | 51 |
| 11.50 | 44 |
| 8.29 | 79 |
| 7.03 | 28 |
| 6.67 | 48 |
| 6.16 | 50 |
| 6.02 | 24 |
| 5.75 | 23 |
| 5.43 | 75 |
| 5.33 | 52 |
| 5.07 | 100 |
| 4.69 | 27 |
| 4.63 | 32 |
| 4.44 | 66 |
| 4.20 | 52 |
| 4.15 | 55 |
| 4.07 | 38 |
| 3.55 | 21 |
| 3.44 | 20 |

Novel Polymorph Form X of Fexofenadine

The Form X of Fexofenadine can be identified by the following characteristics:
a visual melting point (capillary tube) in the range of about 180-188° C.;
a melting endotherm at about 184-189° C. as determined by differential scanning calorimetry;
and an X-ray powder diffraction pattern essentially as shown in the Table 2.

TABLE 2

XRD data of Fexofenadine Hydrochloride Form X polymorph

| D-Space, Angstroms d value | Intensity, $I/I_o$, % $I/Io$ |
|---|---|
| 16.05 | 78 |
| 12.98 | 65 |
| 8.29 | 62 |
| 8.06 | 27 |
| 6.25 | 46 |
| 5.97 | 29 |
| 5.54 | 100 |
| 5.41 | 38 |
| 4.89 | 69 |
| 4.70 | 97 |
| 4.55 | 92 |
| 4.37 | 23 |
| 4.32 | 33 |
| 4.15 | 22 |
| 4.03 | 58 |
| 3.80 | 43 |
| 3.67 | 34 |
| 3.57 | 33 |
| 3.42 | 35 |

The present invention hence offers novel crystalline polymorphs of Fexofenadine and its hydrochloride and also exhibits advantages over prior art methods. Firstly, the present invention provides novel crystalline Fexofenadine, which is of high purity wherein Meta isomer of Fexofenadine is at level below 0.1%.

Moreover, novel crystalline Fexofenadine is also prepared by a cost effective and environment friendly process, which avoids usage of mixture of solvents for recrystallization. Novel anhydrous crystalline polymorphs of Fexofenadine hydrochloride, which is obtained in almost quantitative yield from pure novel crystalline Fexofenadine. Novel anhydrous crystalline Fexofenadine hydrochloride is obtained directly from the novel crystalline Fexofenadine precursor. It is noteworthy to mention that both Fexofenadine and its hydrochloride obtained by the present invention are pure.

The details of the preparation of Fexofenadine polymorphs are described in Indian Patent Application No. 484/MAS/2001 dated Jun. 18, 2001.

The particle size of the Form A and Form X is in the range of 12-18 microns, with not more than (NMT) 10% particles having size 5 microns, NMT 50% particles having size 20 microns, NMT 90% particles having size 50 microns. The mean particle size is 16.36 microns. The bulk density of the Fexofenadine hydrochloride polymorphs is in the range of 0.1-0.2 g/ml.

As used in this specification and in the appended claims the term "therapeutically effective amount of antihistaminic drug" means any drug selected from the group consisting of novel polymorph of Fexofenadine, Loratadine, Terfenadine, Cetrizine or a pharmaceutically accepted salts thereof, preferably novel polymorph of Fexofenadine, more preferably polymorph A or polymorph X of Fexofenadine.

As used in this specification and in the appended claims the term "therapeutically effective amount of decongestant drug" means any drug selected from the group consisting of Psedoephedrine, Phenylephrine, Phenylpropanolamine or a pharmaceutically accepted salts thereof, preferably Psedoephedrine or pharmaceutically accepted salts thereof, more preferably Pseudoephedrine hydrochloride.

It is understood that a therapeutically effective amount of antihistaminic drug is present in Formulation (A), which provides immediate release of the drug/active ingredient, and, a therapeutically effective amount of decongestant drug is present in Formulation (B), which provides sustained release of the drug/active ingredient. As used herein, the term "sustained-release" refers to a property of the pharmaceutical composition wherein the absorption and bioavailability of the active medicament is maintained in a time-release pattern such that therapeutically effective amounts of the decongestant drug are bioavailable over an extended period of time. The term "immediate-release" refers to a property of the pharmaceutical composition wherein the entire dose of active medicament is made bioavailable without substantial delay.

As used in this specification and in the appended claims the term "sustained release compound" refers to the compounds selected from the group consisting of Kollidon SR (a mixture of 80% polyvinyl acetate, 19% povidone, 0.8% SLS and 0.2% collodial silica), Sodium alginate, Xanthan gum, Carbopol, Chitosan, Ethyl cellulose, cellulose ethers, Methacrylic polymers such as Eudragit RL PO, Eudragit RS PO, and such like, which provides the sustained release of the active ingredient form the formulation. It is obvious to the person skilled in the art to replace Kollidon SR with a mixture of polyvinyl acetate and povidone. Such a mixture is also contemplated to be a substitute to Kollidon SR and are contemplated to be within the meaning of Kollidon SR in the appended claims. The active ingredient used in this specification means the one selected from decongestant and antihistaminic drugs as disclosed in this specification.

It is, of course, understood that Formulation (A) and Formulation (B) may contain any of the drug belonging to respective category as described above.

When a decongestant drug is present in Formulation (B) it is preferred that from about 10% to about 40% is present in Formulation (B), more preferably from about 25% to about 30% is present in Formulation (B). When an antihistaminic drug is present in Formulation (A) the amount depends on the drug incorporated.

As used herein and in the appended claims the term "one or more pharmaceutically accepted cellulose derivatives" refers to powdered cellulose, microcrystalline cellulose, "one or more pharmaceutically accepted starch derivatives" refers to corn starch, potato starch, starch 1500, powdered cellulose and such like. The corn starch and powdered cellulose are preferred as starch and cellulose derivatives respectively for the purpose of present invention. The disintegrants used in this specification and in the appended claims are selected from the group consisting of sodium starch glycolate, sodium carboxymethylcellulose, crosslinked polyvinylpyrrolidone, crosscarmellose sodium and such like. The preferred disintegrant as used herein includes crosscarmellose sodium. As used herein and in the appended claims the term "one or more pharmaceutically accepted excipients" refers to commonly used pharmaceutical accepted glidants or lubricants. The preferred lubricants are talc and magnesium stearate and the preferred glidants are talc and colloidal silicon dioxide. The preferred polyols are those selected from mannitol or xylitol.

As used in this specification and in the appended claims the term "suitable coating agent" means any of the commercially used tablet coating agents selected for the groups consisting of sucrose talc, precipitated calcium carbonate, gelatin, acacia, carnauba wax, etc The water soluble film-coating-material includes, for instance, various polymers such as hydroxypropylcellulose, polyethylene glycol, hydroxypropylmethylcellulose, hydroxyethylcellulose, methylhydroxyethylcellulose, etc.; a synthetic polymer such as polyvinylacetal diethylaminoacetate, aminoalkyl methacrylate copolymer E [EUDRAGIT E], polyvinylpyrrolidone, a polysaccharide such as pullulan, etc.;

In a particularly preferred embodiment of the present invention, with respect to antihistaminic drug, about 60 mg of novel polymorph of Fexofenadine (Form A or Form X) or a pharmaceutically accepted salt thereof, is present in Formulation (A) and about 120 mg of psedoephedrine hydrochloride or a pharmaceutically accepted salt thereof, is present in Formulation (B).

The term Allegra-D refers to bilayered tablet commercially available by Aventis, which contains 60 mg Fexofenadine and 120 mg Pseudoephedrine hydrochloride. The term test tablet refers to the tablets prepared in accordance with the present invention.

Dosage forms Containing Fexofenadine Hydrochloride Novel Polymorphs:

The low solubility and physicochemical properties of Fexofenadine hydrochloride imposes the problem in formulation and bioavailability. Moreover, the polymeric conversion is most common still challenging aspect to the formulation scientists to ensure product quality and organoleptic properties. Therefore the selection of proper formulation technique is crucial to ensure better stability and bioavailability of the final dosage form. Following techniques are robust enough to assure the product quality characteristic in routine manufacturing.

Bilayered Tablet Preparation:

The bilayered tablet of the present invention consists of two discreet layers comprising decongestant drug, Psedoepherine hydrochloride in Formulation (B) and antihistaminic drug, novel polymorph of Fexofenadine in Formulation (A). The composition and formulation of each layer is disclosed below.

EXAMPLE 1

| SN | Ingredients | Quantity mg/tablet | Percentage (%) |
|---|---|---|---|
| Step A: Formulation (A) | | | |
| Wet mass preparation | | | |
| 1 | Fexofenadine hydrochloride Form X or Form A | 60.00 | 20.00% |
| 2 | Powered cellulose (Elcema P100) | 55.00 | 18.33% |
| 3 | Mannitol (Pearlitol SD 200) | 26.00 | 8.67% |
| 4 | Corn starch B-700 | 23.33 | 7.78% |
| 5 | Crosscarmellose Sodium | 12.00 | 4.00% |
| 6 | Colloidal silicon dioxide | 4.50 | 1.5% |
| 8 | Iron oxide | 1.50 | 0.5% |
| 9 | Isopropyl alcohol | qs | qs |
| Lubrication | | | |
| 10 | Powered cellulose (Elcema G250) | 54.00 | 18.00% |
| 11 | Mannitol (Pearlitol DC 400) | 26.67 | 8.89% |
| 12 | Corn starch B-700 | 20.33 | 6.78% |
| 13 | Crosscarmellose Sodium | 12.00 | 4.00% |
| 14 | Colloidal silicon dioxide | 1.67 | 0.56% |
| 15 | Magnesium stearate | 3.00 | 1.00% |
| | Total | 300.00 | 100% |

Sift Fexofenadine hydrochloride (Form X/A), mannitol, powdered cellulose, crosscarmellose sodium and collodial silicon dioxide through mesh #20 screen. Sift corn starch iron oxide red through mesh #80 screen. Mix the sifted material in rapid mixer granulator (RMG) for about 25 minutes. Mix the obtained dry mix from RMG with isopropyl alcohol to obtain desired wet mass. Dry the material in fluidized bed drier. Collect the mesh #24 (screen) oversize fraction after sifting the dried material and mill using 1.5 mm screen in comminuting mill. Sift powdered cellulose, mannitol and corn starch through mesh #20 screen. Colloidal silicon dioxide, crosscarmellose and magnesium stearate are sifted through mesh #40 screen. Mix the sifted and milled Fexofenadine hydrochloride material with the above sifted material in double cone blender for about 15 minutes. The dried blend is then used for compressing into tablets.

| SN | Ingredients | Quantity mg/tablet | Percentage (%) |
|---|---|---|---|
| Step B: Formulation (B) | | | |
| 1 | Pseudoephedrine hydrochloride | 120 | 30.00% |
| 2 | Kollidon- SR | 270 | 67.5% |
| 3 | Magnesium stearate | 4.5 | 1.13% |
| 4 | Colloidal silicon dioxide | 5.5 | 1.37% |
| | Tablet weight | 400 mg | 100% |

Sift Pseudoephedrine hydrochloride, Kollidon SR, colloidal silicon dioxide through #60 screen. Mix all the ingredients in a suitable blender for about 20 minutes. Sift magnesium stearate through mesh #40 screen and mix with above blend in a suitable blender for about 5 minutes. The blend thus prepared is used for compression into tablets.

Step C: Tablet Compression

The granulation prepared from Formulation (A) and Formulation (B) is pressed into a suitable tablet press for preparing conventional multi layer tablets. A bilayered tablet is prepared from Formulation (B) compressed first with a hardness of 2-4 kp (Vankel) and average weight of 380-420 mg followed by compression of Formulation (A) onto the first layer resulting in tablets with an average weight of 685-715 mg and hardness of 14-20 kp.

Step D: Aqueous Coating Suspension

The tablets prepared in step (C) is coated with a transparent coat comprising of HPMC and PEG 600/Triethyl citrate dispersion prepared in purified water with about 2-3% build-up by weight resulting in tablets with average weight of 710-730 mg.

Dissolution Profile of Allegra-D vs Test Tablet

The dissolution of Fexofenadine from first discrete layer and Psedoepherine hydrochloride from second discrete zone is given in following Table.

EXAMPLE 1

Apparatus: USP-I (Basket), Media: 0.001N HCL, RPM: 100 RPM.

| % Drug Release | | | | | | | | | | | |
|---|---|---|---|---|---|---|---|---|---|---|---|
| Fexofenadine Hydrochloride (Formulation A) | | | Pseudoephedrine Hydrochloride (Formulation B) | | | | | | | | |
| 15 min | 30 min | 1 hr | | 15 min | 30 min | 1 hr | 3 hrs | 5 hrs | 7 hrs | 10 hrs | 12 hrs |
| Allegra -D 86 | 93 | 101 | Allegra -D | 18 | 24 | 33 | 56 | 67 | 76 | 85 | 88 |
| Test Tablets A 100 | 99 | 105 | Test Tablets B | 18 | 25 | 36 | 56 | 68 | 77 | 85 | 89 |

Test Tablet A: Contains Fexofenadine Form A/X
Test Tablet B: Contains Pseudoephedrine Hydrochloride The present invention provides a dissolution profile comparable to Allegra-D.

Pharmacokinetic Profile

When the pharmacokinetic profile of the test product is compared with that of innovator's product (Allegra-D), the pharmacokinetic parameters (AUC, Cmax, Tmax) are found to be comparable (Least square mean ratio: Test: Reference is within 80% to 125%)

The controlled drug release of Psedoephedrine hydrochloride over 12 hour post dosing has been similar in both the test and the reference formulations and the plasma concentration are above the minimum therapeutic level. (100 ng.ml)

Fexofenadine pharmacokinetic demonstrate a comparable immediate drug release profile for test and reference formulations.

In the preliminary clinical studies (Bioequivalence) there were no adverse drug reactions reported and both the formulations were without any serious side effects in the population tested. The details of the pharmacokinetic data obtained are presented below.

Pseudoephedrine Hydrochloride:

|  | AUC ng · hr · ml$^{-1}$ (n = 12) | Cmax ng · ml$^{-1}$ (n = 12) |
|---|---|---|
| Test | 5515.69 (35.57) | 393.21 (24.75) |
| Allegra-D (Reference) | 5164.44 (35.29) | 400.51 (27.66) |
| Ratio of least square means (T/R) % | 106.80 (38.37) | 98.18 (15.30) |

Fexofenadine Hydrochloride:

|  | AUC ng · hr · ml$^{-1}$ | Cmax ng · ml$^{-1}$ (n = 12) |
|---|---|---|
| Test | 1862.27 (46.82) | 300.11 (37.8) |
| Allegra-D (Reference) | 1624.01 (66.70) | 251.85 (50.2) |
| Ratio of least square means (T/R) % | 114.67 (35.52) | 119.17 (39.54) |

Stability Data of Test Tablets:

The stability studies were carried out at 40° C. and 75% relative humidity (40/75)

| Assay | | | | |
|---|---|---|---|---|
| | | Time | | |
| | Initial | 1 Month | 2 Months | 3 Months |
| Fexofenadine hydrochloride | 110.7 | 103.8 | 103.5 | 113.1 |
| Pseudoephedrine hydrochloride | 97.6 | 94.8 | 94.3 | 93.9 |

| Related substances | | | | |
|---|---|---|---|---|
| | | Time | | |
| | Initial | 1 Month | 2 Months | 3 Months |
| Fexofenadine hydrochloride | | | | |
| % Maximum individual Impurity | 0.0602 | 0.0734 | 0.0375 | 0.035 |
| % Total Impurity | 0.2990 | 0.2965 | 0.2338 | 0.2533 |
| Pseudoephedrine hydrochloride | | | | |

-continued

Related substances

| | Time | | | |
|---|---|---|---|---|
| | Initial | 1 Month | 2 Months | 3 Months |
| % Maximum individual Impurity | 0.0509 | 0.0516 | 0.0416 | .01910 |
| % Total Impurity | 0.2214 | 0.2314 | 0.2213 | 0.2743 |

Dissolution:

| | Time | | | |
|---|---|---|---|---|
| | Initial | 1 Month | 2 Months | 3 months |
| Fexofenadine hydrochloride | | | | |
| 60 minutes | 93 | 97 | 99 | 100 |
| Pseudoephedrine hydrochloride | | | | |
| 1 hr | 37 | 30 | 28 | 26 |
| 2 hrs | 63 | 49 | 43 | 42 |
| 5 hrs | 79 | 65 | 56 | 56 |
| 12 hrs | 103 | 90 | 85 | 90 |

EXAMPLE 2

Step A: Formulation (A)

| SN | Ingredients | Quantity mg/tablet |
|---|---|---|
| 1 | Fexofenadine hydrochloride Form A | 60.00 |
| 2 | Powered cellulose (Elcema G250) | 108.00 |
| 3 | Mannitol (Pearlitol DC 400) | 54.00 |
| 4 | Corn starch B-700 | 43.00 |
| 5 | Colorant | 1.50 |
| 6 | Isopropyl alcohol | Q.S. |
| 7 | Crosscarmellose Sodium | 24.00 |
| 8 | Magnesium stearate | 3.00 |
| 9 | Colloidal silicon dioxide | 6.50 |
| | Tablet weight | 300 |

The procedure is similar to that described in Example 1.
Step B: Formulation (B)

| SN | Ingredients | Quantity mg/tablet |
|---|---|---|
| 1 | Pseudoephedrine hydrochloride | 120 |
| 2 | Kollidon- SR | 270 |
| 3 | Magnesium stearate | 4.5 |
| 4 | Colloidal silicon dioxide | 5.5 |
| | Tablet weight | 400 mg |

The procedure is similar to that described in Example 1.
The examples are explanatory only and should not be construed to limit the scope of the invention in any way. Many modifications are obvious to those skilled in the art and are contemplated to be within the scope of the appended claims.

We claim:

1. A pharmaceutical composition comprising:
   a) a tablet layer comprising an antihistaminic drug, a cellulose derivative, a polyol, a starch derivative, and a disintegrant; and
   b) a tablet layer comprising a decongestant drug and a sustained release compound.

2. The pharmaceutical composition of claim 1, wherein an antihistaminic drug comprises crystalline Form X of fexofenadine hydrochloride.

3. The pharmaceutical composition of claim 1, wherein a cellulose derivative comprises powdered cellulose, microcrystalline cellulose, or a mixture thereof.

4. The pharmaceutical composition of claim 1, wherein a polyol comprises mannitol, xylitol, or a mixture thereof.

5. The pharmaceutical composition of claim 1, wherein a starch derivative comprises corn starch, potato starch, starch 155, or a mixture of any two or more thereof.

6. The pharmaceutical composition of claim 1, wherein a disintegrant comprises sodium starch glycolate, sodium carboxymethylcellulose, crosslinked polyvinylpyrrolidone, croscarmellose sodium, or a mixture of any two or more thereof.

7. The pharmaceutical composition of claim 1, wherein a decongestant drug comprises pseudoephedrine, phenylephrine, phenylpropanolamine, a pharmaceutically acceptable salt of any of the foregoing, or a mixture of any two or more thereof.

8. The pharmaceutical composition of claim 1, wherein a sustained release compound comprises: a mixture comprising polyvinyl acetate and povidone; sodium alginate; xanthan gum; carbopol; chitosan; ethyl cellulose; a cellulose ether; a methacrylic polymer; or a mixture of any two or more thereof.

9. The pharmaceutical composition of claim 1, wherein an antihistaminic drug comprises crystalline form X of fexofenadine hydrochloride and a decongestant drug comprises pseudoephedrine or a salt thereof.

10. A pharmaceutical composition comprising:
    a) a tablet layer comprising an antihistaminic drug, cellulose, mannitol, starch, and croscarmellose sodium; and
    b) a tablet layer comprising a decongestant drug and a mixture of polyvinyl acetate and povidone.

11. The pharmaceutical composition of claim 10, wherein an antihistaminic drug comprises crystalline form X of fexofenadine hydrochloride.

12. The pharmaceutical composition of claim 10, wherein a decongestant drug comprises a salt of pseudoephedrine.

13. The pharmaceutical composition of claim 10, wherein tablet layer a) comprises about 20 to about 45 percent by weight cellulose.

14. The pharmaceutical composition of claim 10, wherein tablet layer a) comprises about 10 to about 30 percent by weight mannitol.

15. The pharmaceutical composition of claim 10, wherein tablet layer a) comprises about 5 to about 25 percent by weight starch.

16. The pharmaceutical composition of claim 10, wherein tablet layer a) comprises about 4 to about 15 percent by weight croscarmellose sodium.

17. The pharmaceutical composition of claim 10, wherein tablet layer b) comprises about 40 to about 80 percent by weight of a mixture of polyvinyl acetate and povidone.

18. The pharmaceutical composition of claim 10, wherein tablet layer b) comprises about 40 to about 80 percent by weight of a mixture comprising about 80 percent polyvinyl acetate and about 19 percent povidone.

19. The pharmaceutical composition of claim 10, wherein tablet layer b) is formed by compressing granules comprising a decongestant drug and a mixture of polyvinyl acetate and povidone, about 5-15 percent of the granules being retained on an 80 mesh sieve, about 10-25 percent of the granules being retained on a 100 mesh sieve, and about 80-95 percent of the granules being retained on a 200 mesh sieve.

20. A pharmaceutical composition comprising:
   a) a tablet layer comprising crystalline form X of fexofenadine hydrochloride, about 20 to about 45 percent by weight cellulose, about 10 to about 30 percent by weight mannitol, about 5 to about 25 percent by weight starch, and about 4 to about 15 percent by weight of a disintegrant; and
   b) a tablet layer comprising a salt of pseudoephedrine and about 40 to about 80 percent by weight of a mixture comprising about 80 percent polyvinyl acetate and about 19 percent povidone.

* * * * *